(12) United States Patent
Edwards et al.

(10) Patent No.: US 6,911,027 B1
(45) Date of Patent: Jun. 28, 2005

(54) DEVICE FOR THE ABLATION OF TISSUE

(75) Inventors: Stuart D. Edwards, Portola Valley, CA (US); James A. Filice, Los Gatos, CA (US); Benjamin T. Nordell, Menlo Park, CA (US); Brian O. Armijo, Mountain View, CA (US)

(73) Assignee: Somnus Medical Technologies, Inc., Sunnyvale, CA (US)

( * ) Notice: Subject to any disclaimer, the term of this patent is extended or adjusted under 35 U.S.C. 154(b) by 0 days.

(21) Appl. No.: 09/302,055

(22) Filed: Apr. 29, 1999

Related U.S. Application Data (63) Continuation of application No. 08/912,273, filed on Aug. 15, 1997, now Pat. No. 6,102,907.

(51) Int. Cl.$^7$ ............................................... A61B 18/18
(52) U.S. Cl. ............................. 606/40; 606/49; 606/41; 604/22
(58) Field of Search ............................... 606/34, 37–42, 606/44, 45–50; 607/101, 102, 115, 116

(56) References Cited

U.S. PATENT DOCUMENTS 4,802,476 A * 2/1989 Noerenberg et al.
5,762,626 A * 6/1998 Lundquist et al. ............ 604/22
5,843,021 A * 12/1998 Edwards et al. .............. 604/22
5,871,481 A * 2/1999 Kannenberg et al. ......... 606/34

* cited by examiner

Primary Examiner—Linda C. M. Dvorak
Assistant Examiner—Roy Gibson
(74) Attorney, Agent, or Firm—Flehr Hohbach Test Albritton & Herbert LLP

(57) ABSTRACT

A device for the ablation of tissue for use with the fingers of a human hand and a radio frequency power supply and controller providing a source of radio frequency energy and controls for controlling the application of radio frequency energy to the device comprising a handle sized so that is adapted to be grasped and supported by the human hand and having proximal and distal extremities. A single conductive needle formed of a conducting material is disposed in the distal extremity of the handle. An edge card is mounted in the handle and has edge mounted contacts with circuitry connected thereto. An edge mount board connector is mounted in the handle and is removably secured to the edge mounted contacts of the edge card. A cable is connected to the edge mount connector and extends from the proximal extremity of the handle and is adapted to be coupled to the radiofrequency power supply and controller. A second printed circuit board is mounted in the handle in a spaced-apart position from the edge card. A flex cable having conductive leads carried thereby extends between the edge card and the printed circuit board and is physically and electrically connected to the edge card. The proximal extremity of the needle is secured to the printed circuit board and makes electrical connections therewith.

13 Claims, 4 Drawing Sheets

DEVICE FOR THE ABLATION OF TISSUE

This is a continuation-in-part of application Ser. No. 08/912,273 filed on Aug. 15, 1997, now U.S. Pat. No. 6,102,907.

This invention relates to an apparatus and device for use therein and a method for ablation of tissue and more particularly to the treatment of tissue in the human body as for example the uvula, tonsils, adenoids, sinus tissue, tongue and turbinates.

Apparatus, device for use therein and methods for ablating tissue have heretofore been provided. However it has been found that for some applications, they are unduly complicated and expensive. There is therefore a need for a simplified tissue ablation device which will meet the requirements for tissue ablation and be less expensive.

In general it is an object of the present invention to provide an apparatus and device for use therein and a method for the ablation of tissue which incorporates a simplified tissue ablation device.

Another object of the invention is to provide an apparatus, device and method of the above character which can utilize a less expensive simplified tissue ablation device.

Another object of the invention is to provide a device of the above character which is shaped to provide improved viewing capabilities for the physician using the device.

Another object of the invention is to provide a device of the above character which has been ergonomically shaped for improved grasping by the hand of the physician.

Another object of the invention is to provide a device of the above character in which a straight needle shape is maintained so that the device can only be utilized for straight entry applications.

Another object of the invention is to provide a device of the above character in which an edge mounted on a printed circuit board is utilized.

Another object of the invention is to provide a device of the above character in which a flexible cable is utilized for making connections to the needle.

Another object of the invention is to provide an apparatus and device for use therewith in which a substantial portion of the device can be reused.

Another object of the invention is to provide a device of the above character in which the reusable portion includes the cabling connected to the device.

Another object of the invention is to provide a device of the above character in which the throwaway parts of the device have been reduced to a minimum.

Another object of the invention is to provide a device of the above character which is light in weight and which can be readily used.

Additional objects and features of the invention will appear from the following description in which the preferred embodiments are set forth in detail in conjunction with the accompanying drawings.

In general, the device for ablation of tissue is for use with the human hand and with a radio frequency controller providing a source of radio frequency energy and means for controlling the application of radio frequency energy to the device. It comprises a handle sized so as adapted to be grasped by the human hand and has proximal and distal extremities. A needle formed of a conductive material and having proximal and distal extremities is provided. Means is provided for mounting the proximal extremity of the needle on the distal extremity of the handle so that it is insulated from the handle. The conductive means is carried by the handle and is connected to the needle and extends from the handle and is adapted to be coupled to the radio frequency controller for supplying radio frequency energy to the needle. Means is carried by the handle and is adapted to be coupled to the radio frequency power supply and controller for sensing the application of radio frequency energy to the tissue and for controlling the application of radio frequency energy to the needle.

Figure 1:
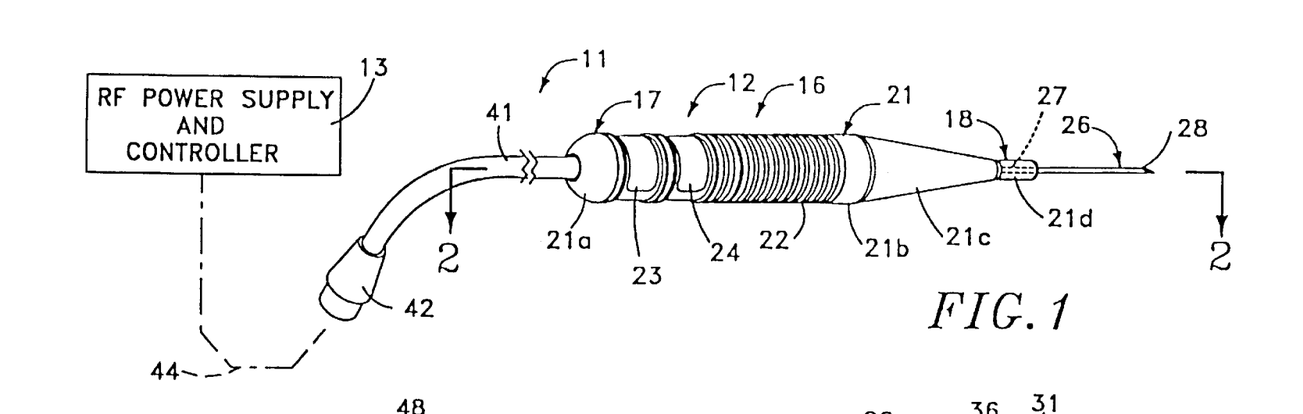
FIG. 1 is an isometric view of one embodiment of an apparatus and device for use therein for the ablation of tissue incorporating the present invention.

More in particular, the apparatus 11 of device 12 for use therein for the ablation of tissue as shown in FIG. 1 includes the hand held device 12 and a radio frequency power supply and controller 13 as shown in block form.

The device 12 consists of a handle or housing 16 which is to size so that it is adapted to be grasped by the human hand or at least by two fingers of the human hand. The handle or housing 16 is formed of a suitable material such as a plastic which is molded into a desired shape as for example, generally cylindrical as shown in FIG. 1 and is provided with proximal and distal extremities 17 and 18. The handle 16 is provided with an outer surface 21 with a semi-hemispherical portion 21a provided on the proximal extremity, a cylindrical portion 21b extending from the proximal extremity for a distance of approximately 2½", a tapered or conical portion 21c having a length of approximately 1½" and a smaller diameter cylindrical portion 21d having a length of approximately ½". The handle 16 can be of a suitable diameter such as ½". It should be appreciated that if desired rather than it being circular in cross section, the handle 16 can be rectangular in cross section. A portion of the surface 21b is provided with a plurality of circumferentially extending annular grooves 22 spaced apart longitudinally of the central axis of the handle 16 to facilitate gripping of the handle by the fingers of a human hand. A pair of spaced apart annular recesses 23 and 24 is provided on which identification labels (not shown) can be placed.

Figures 2, 3, 4:
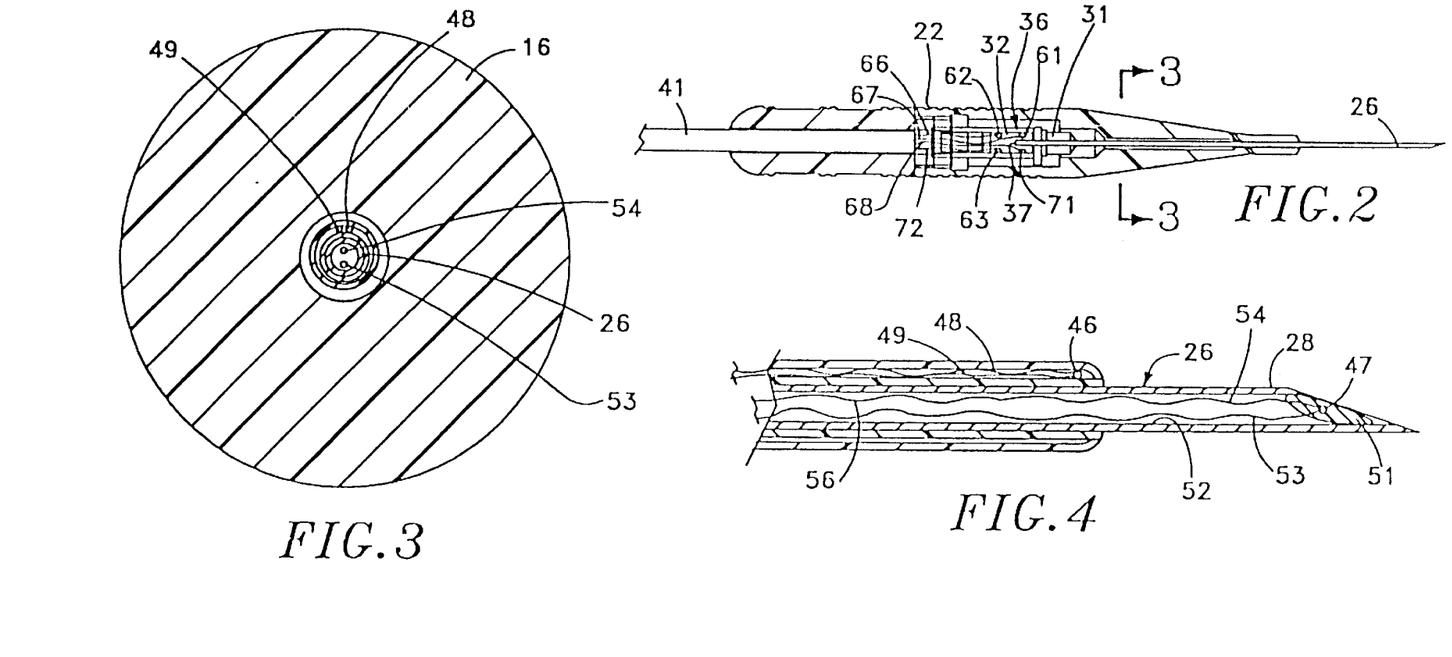
FIG. 2 is a cross-sectional view taken along the line 2—2 of FIG. 1.
FIG. 3 is a cross-sectional view taken along the line 3—3 of FIG. 2.
FIG. 4 is an enlarged detail view of the distal extremity of the device shown in FIGS. 1 and 2.

A sharpened needle 26 is provided which has proximal and distal extremities 27 and 28. It is formed of a suitable conductive material such as stainless steel which is capable of delivering radio frequency energy. Means is provided for mounting the needle in the handle or housing 16 so that it is static or nondeployable. As shown in FIGS. 1 and 2, it is mounted on the distal extremity 18 by being molded directly into the plastic handle or housing 16. The proximal extremity 27 of the needle 26 is mounted in a carrier 31 formed of a suitable material such as plastic which is mounted within the handle 16 as shown in FIG. 2. A printed circuit board 32 is mounted on the carrier 31 immediately adjacent the proximal extremity 27 of the needle 26.

Conductive means 36 is carried by the handle and is connected to the needle and is adapted to be coupled to the radio frequency power supply and controller 13 for supplying radio frequency energy to the needle 26. Typically this conductive means takes the form of a single conductor 37 hereinafter described which is coupled to the needle 26 by suitable means such as solder and which extends proximally through the housing and to a flexible cable 41 secured to the proximal extremity of the handle 16. The flexible cable 41 carries a male adapter 42 which is adapted to be coupled to a female adapter (not shown) to a cable 44 to the radio frequency power supply and controller 13.

Means is carried by the handle or housing 16 and is adapted to be coupled to the radio frequency power supply and controller 13 for sensing the application of radio frequency energy as it is supplied by the needle 26 to the tissue in the human body for controlling the application of radio frequency energy to the tissue and consists of at least one device for sensing temperature and/or impedance. Thus as shown there are provided first and second thermocouples 46 and 47. In accordance with the present invention, the first thermocouple 46 as shown in FIG. 4 is mounted in the distal extremity 18 of the handle 16 and is provided for sensing the temperature of the tissue in the immediate vicinity of the thermocouple 46 adjacent to an intermediate portion of the needle 26 where it enters the handle 16, as for example approximately 20 millimeters from the end of the needle 26. First and second conductors 48 and 49 are provided which are connected to the thermocouple 46. If desired, the conductors 48 and 49 alternatively can be secured to the needle 26 by a shrink tube (not shown) secured to the handle 16. The other or second thermocouple 47 is mounted in the distal extremity 28 of the needle 26 and as shown can be supported by an epoxy 51 provided in a bore 52 in the needle 26 extending longitudinally of the needle 26. The epoxy 51 in addition to holding the thermocouple 47 seals off the lumen or bore 52. The thermocouple 47 senses the temperature of the tissue in the immediate vicinity of the distal extremity 28 of the needle 26. First and second conductors 53 and 54 connected to the thermocouple 47 extend proximally within the bore 52 of the needle 26 from the thermocouple 47. The conductors 48 and 49 and the conductors 53 and 54 extend proximally to the printed circuit board 32 as shown in FIG. 2 and terminate in three contacts 61, 62 and 63 provided on the printed circuit board 32 in which contact 62 is a common contact to which are bonded conductors 66, 67 and 68 which extend into the cable 41. Another contact 71 is provided on the printed circuit board 32 which is connected to the needle 26 by the conductor 37 which is also connected to a conductor 72 extending into the cable 41. These conductors 66, 67, 68 and 72 are connected into the radio frequency power supply and controller 13 and are utilized for supplying radio frequency energy to the needle electrode 26 and for the control of the radio frequency power supply and controller 13 in accordance with the parameters, i.e. temperatures, being sensed by at least one thermocouple and preferably both thermocouples 46 and 47.

Since the needle 26 is a static or nondeployable needle, the needle 26 upon manufacture of the device 12 can be selected to be of a suitable length projecting distally from the distal extremity 18 of the handle 16. Thus a needle having a length ranging from 15 to 30 mm and preferably approximately 20 mm can be readily provided. The needle can be of a certain size as for example 23-gauge.

It should be appreciated that insulation can be extended on the needle so that a desired active length for the needle is provided for supplying radio frequency energy to the tissue.

Operation and use of the apparatus and the device for use therewith may now be briefly described as follows. Assuming that the device 12 has been connected to the radio frequency power supply and controller 13, the physician doing the desired tissue ablation procedure grasps the handle 16 of the device by the fingers of a hand or in the palm of the hand and with a straight needle 26 as shown in FIG. 1, the physician can utilize the handle to cause the needle to penetrate the tissue it is desired to ablate. The needle 26 is positioned so that the insulation engaging the proximal end of the needle 26 is well past the mucosal layers of the tissue, after which the radio frequency power supply and controller 13 can be turned on. This ensures that the mucosal layer will remain undamaged and will not be thermally ablated.

The needle 26 can be utilized as a unipolar device with a grounding pad (not shown) being provided on the patient as for example on the back of the patient to complete the circuit for the radio frequency energy from the radio frequency power supply and the return to the radio frequency power supply 13. For example with a straight needle, the turbinates can be readily treated with the device 12. The treatment can be carried out for an appropriate length of time from 20 seconds to 5 minutes with the radio frequency energy being applied at the desired frequency, as for example a frequency of 580 kilohertz and a power level ranging from 5 to 50 watts. The shorter times are desirable where the size of the anatomical feature to be treated is small (such as the uvula) or where the tissue is highly hydrated or perfused. This helps to preserve anatomical tissue in the region to be ablated, as for example anatomical features which are then in cross-section (i.e., mucosal membranes). The thermocouples 46 and 47 can be utilized for automatically terminating the application of radio frequency power when a certain temperature in the tissue has been reached as sensed by either one or both of the thermocouples 46 and 47. The delivery of radio frequency energy to the needle 26 is terminated before the needle 26 is withdrawn from the tissue to avoid surface layer thermal damage. After the procedure has been completed, the physician can withdraw the device 12 and can further proceed with the procedure by inserting the needle 26 of the device 12 into another location using the same procedure. The foregoing steps can be repeated as necessary to complete the desired ablation of the tissue being treated.

In the case of some smaller anatomical features, the physician may use lower power levels to obtain a lesion of sufficient size without premature desiccation of the tissue surrounding the active electrode (needle). This lower rate of energy delivery is an important aspect of the present invention because it yields larger lesions and greater volume per penetration than would occur if the power settings were higher. In that case, rapid heating can result in loss of current delivery due to tissue desiccation. The reason the lower power settings result in larger lesions is that the hydrated tissue exhibits thermal conductivity at a fairly inefficient level, but is nonetheless somewhat thermally conductive. If the power setting is appropriate, the tissue is able to conduct the energy outwardly in the form of heat and the tissue immediately adjacent to the active electrode will be kept below the temperature of vaporization of the fluid within the tissue. When vaporization occurs, there is a fluctuation of the ohmic impedance to current low and the tissue rapidly desiccates, resulting in interruption of the circuit. This loss of current flow due to overheating of the tissue adjacent to the electrode needle can be an advantage in that it is a safety aspect of the present invention. For instance, in the event of inadvertent setting of the power at a high level, the rapid desiccation of the thin layer of cells in contact with the active electrode will break the circuit and act as a "biologic switch", cutting off current flow and preventing extensive tissue damage. Only by setting the power at lower levels, as for example 1 watt, can larger lesions be attained. Typically, power settings up to 15 watts are used with the type of device described in the present invention. Situations where power levels as high as 50 or 100 watts can occur where an electrode with a significantly larger surface area is used or where the tissue is highly perfused and the circulatory (blood flow) rate is high, resulting in efficient cooling of the tissue being treated.

For performing other tissue ablation procedures where a curved or bent needle 26 is desired, the needle 26 can be formed of a malleable material and can be bent in a suitable manner to the desired configuration to match the anatomy, as for example the treatment of tonsils, adenoids and sinus tissue. A straight needle can be utilized for treating the uvula.

After the device has been used, it can be disposed of because the device has been designed for a one time use even though the device is manufactured in such a way that it is sterilizable. However, sterilizing the same may be undesirable when it is difficult to ensure that sufficient sterilization has been accomplished and particularly if blood has coagulated on the needle 26 causing a protein buildup which may not be removed during the sterilization procedure. It should be appreciated as hereinbefore explained that the device can still be further simplified by using only one thermocouple. It is possible to utilize only one thermocouple by estimating the temperature gradient which normally occurs between the first and second thermocouples. By utilizing only the first thermocouple 46 it is possible to go to a solid wire for the needle 26 rather than a needle which has a lumen or bore therein.

Figure 5:
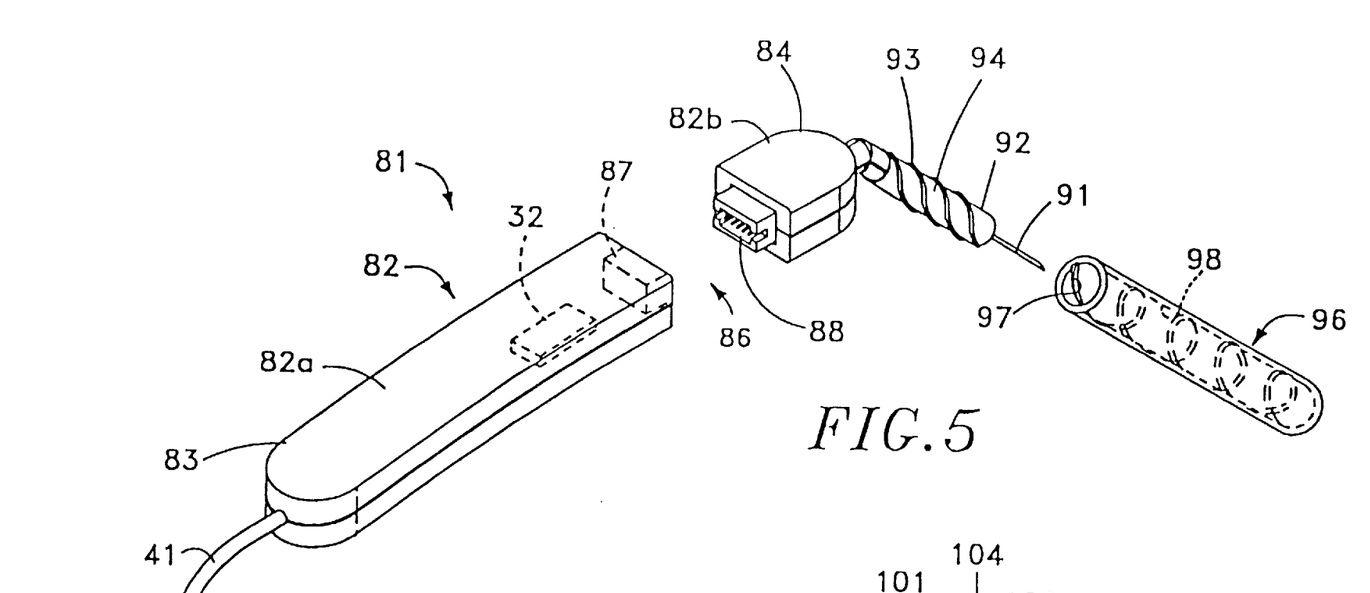
FIG. 5 is an isometric view of another embodiment of a device incorporating the present invention.

In order to still further reduce the cost of the device utilized in connection with the present apparatus, another embodiment of the device is shown FIG. 5 in which the cable and connector are removably mounted on the device as part of the device so that they can be disconnected and only a part of the device disposed of after use. Thus as shown in FIG. 5 there is provided a device 81 which consists of a handle 82 sized to fit into a human hand and which has generally the same configuration as the handle 16, but which is generally rectangular in cross-section rather than circular. It is provided with proximal and distal extremities 83 and 84. The proximal extremity 83 of the housing has mounted therein the cable 41 hereinbefore described in the embodiment shown in FIGS. 1–4. The handle 82 is fabricated in two parts 82a and 82b with the part 82a forming the proximal extremity 83 and the part 82b forming the distal extremity 84. The printed circuit board 32 forming a part of the previous embodiment is also included in the present embodiment with the associated wiring (not shown) and is mounted in the reusable connector portion 82a of the handle 82. A connector assembly 86 is mounted in the two parts 82a and 82b and typically as shown can consist of a female connector 87 mounted in the reusable connector portion 82a and a male connector 88 mounted in the disposable portion 82b.

A needle 91 is mounted in the distal extremity 84 in the manner hereinbefore described in connection with the embodiment shown in FIG. 1. In the embodiment shown, the needle 91 is inclined at an angle with respect to the central axis of the handle 82 as for example at an angle of 45°. An insulating sleeve 92 is provided on the needle and has a length so that the exposed end of the needle 91 extends for a suitable distance as for example 15 to 30 mm and preferably approximately 20 mm. The insulating sleeve 92 is provided with a thread 93 on its exterior surface 94. The threads 93 can be relatively coarse, as for example a quarter pitch, so that a protective sleeve 96 with internal threads 97 in a bore 98 matching the threaded exterior surface 93 can be threaded onto and threaded off of the insulating sleeve 92 with four to five turns of the protective sleeve 96. The protective sleeve 96 can be formed of a suitable material such as plastic. The protective sleeve 96 has a length so that it will extend over the length of the insulating sleeve 92 and still provide adequate space for the needle 91 extending distally from the insulating sleeve 92.

It can be seen that by providing a threaded protective sleeve 96, the sleeve 96 can be rotated for removal of the same. This threaded arrangement is preferable to one which is mounted by a slip fit because a slip fit requires movement of the sleeve towards and away from the needle during pushing and pulling of the sleeve, making it possible for the physician using the same to inadvertently be punctured by the needle.

The device shown in FIG. 5 can be used in a manner very similar to that hereinbefore described with respect to the previous embodiment. After the device has been used, the portion 82b can be separated from the portion 82a and only the portion 82b disposed of after use. The remaining portion 82a with the cable 41 can be retained for future reuse. This part 82a can be readily sterilized if necessary and carries the carrier components which comprise the major expense in fabricating the handle 81. Thus it can be seen that such a construction makes it possible to further reduce the cost of the device utilized in the apparatus of the present invention.

Figure 6:
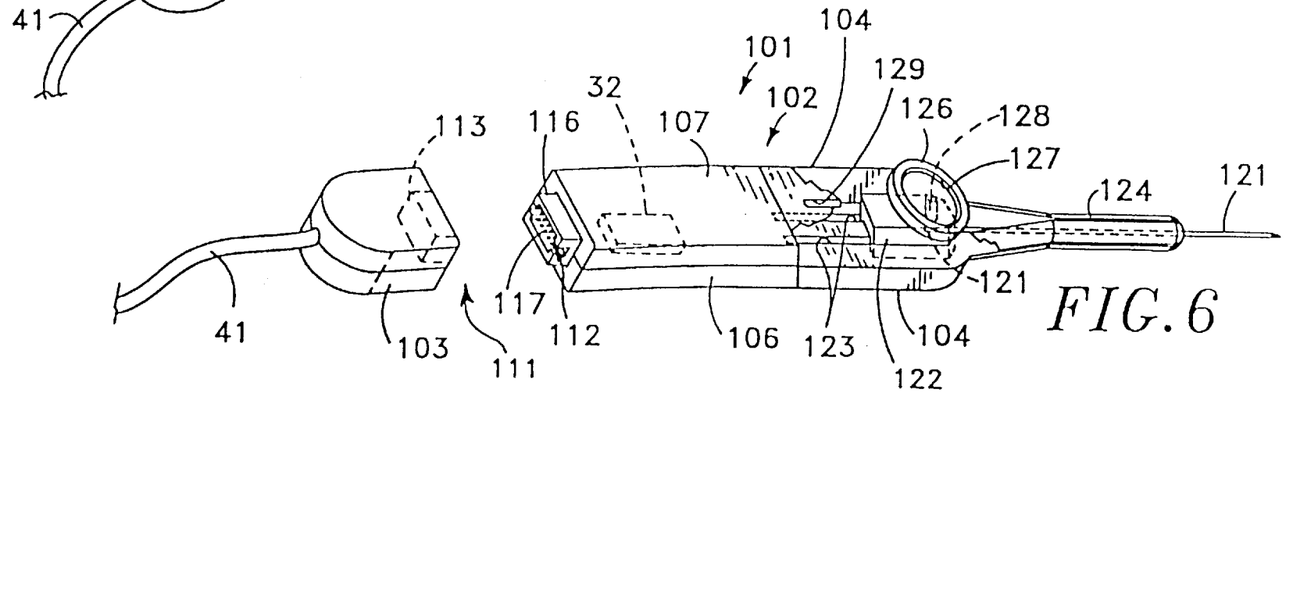
FIG. 6 is an isometric view of another embodiment of a device incorporating the present invention.

Still another embodiment incorporating the device of the present invention is shown in FIG. 6 which is slightly more expensive than that shown in FIG. 5, but however retains as a separable part the connector and cable forming a part of the handle. Thus as shown in FIG. 6 there is provided a device 101 which is also sized to fit into the human hand but typically is larger so that it is adapted to be held in the palm of the hand while a finger or fingers are utilized for operating the device. The handle 102 as shown is rectangular in cross section and is provided with proximal and distal extremities 103 and 104 with the proximal extremity 103 comprising the reusable part and the distal extremity 104 comprising the disposable part. The handle or housing 102 is formed of a suitable material such as plastic with lower and upper parts 106 and 107 which are fastened together in a suitable manner such as by an adhesive or by ultrasonic bonding. A connector assembly 111 is provided for connecting the wires or conductors utilized in the device and consists of a male connector 112 provided in a distal extremity 104 and a female connector 113 provided in the proximal extremity or reusable portion 103. The male connector assembly is provided with a rectangular framework 116 formed of a suitable material such as plastic to prevent accidental contact with the pins 117 forming a part of the male connector assembly 112. The female connector assembly 113 is connected to the cable 41 connected to the reusable proximal part 103.

A retractable needle 121 is carried by the handle or housing 102 and is mounted on a slider 122 movable in slots 123 within the handle 102 from a distal extremity where the needle is in an extended position extending beyond a cylindrical insulation sleeve 124 forming a part of the handle 102 and a retracted position in which the needle is completely retracted within the insulation sleeve 124. Movement of the slider 122 is under the control of a circular knob 126 slidably mounted on the exterior of the handle or housing 102 and adapted to be grasped by a finger of the hand and particularly the thumb of the hand holding the device 101. The knob is provided with a centrally disposed recess 127 adapted to be engaged by the thumb of the holding hand. The circular knob 126 is provided with a depending stem 128 which extends through a slot 129 in the top cover 107. The slot 126 extends longitudinally of the top cover 107 along the central axis of the handle or housing 102. A printed circuit board 32 of the type hereinbefore described is mounted within the handle 102 and is provided with folded wires or conductors (not shown) which permit the slider 122 to move between extended and retracted positions while still continuing to receive information from the thermocouples and also to supply radio frequency energy to the needle 121.

Operation and use of the device 101 shown in FIG. 6 is very similar to that hereinbefore described. However, in many respects it is more user friendly than the other embodiments of the device herein disclosed. For example by providing a retractable needle 121, it is possible for the physician to position the needle in the desired position merely by engaging the knob 126 by the thumb of the hand while the same hand is holding the device to advance the needle 121 into the tissue to be treated. After the application of radio frequency energy in the manner hereinbefore described, the needle 121 can be retracted back into the handle 102 without danger of the physician being pricked by the needle. The major portion of the device can still be saved by separating the proximal portion 103 which carries the cable 41 from the distal portion 104 so that the distal portion can thereafter be disposed of after a one-time use.

Another embodiment of a device incorporating the present invention is shown in FIGS. 7–10. As shown therein, there is provided a device 141 which is provided with a handle 142 which is adapted to be grasped between the fingers of a human hand for use of the device. The handle 142 is formed with a two-part housing 143 having a main housing 146 and a connector housing 147. The main housing 146 is provided with mating top and bottom casings 146a and 146b and similarly, the connector housing 147 is provided with mating top and bottom covers 147a and 147b. The housing 143 can be formed of a suitable material such as plastic with the top and bottom casings 146a and 146b being fastened together in a suitable manner such as by ultrasonic bonding. Similarly, the top cover 147a and the bottom cover 147b can be fastened together in a similar manner. The handle 142 is provided with proximal and distal extremities 151 and 152.

Figures 7, 8:
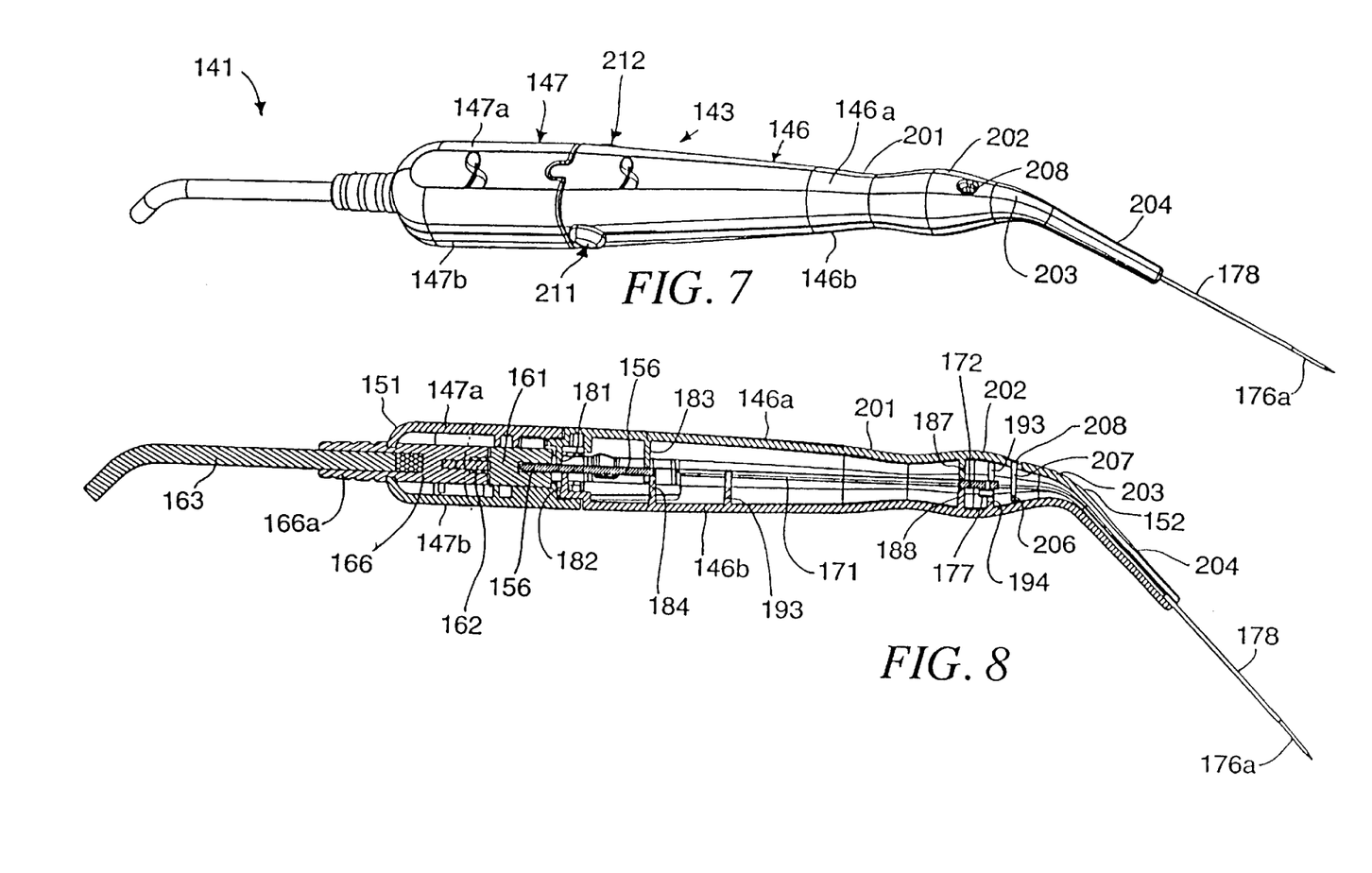
FIG. 7 is an isometric view of another embodiment of a device incorporating the present invention.
FIG. 8 is a sectional view taken of the device as shown in FIG. 7.

An edge card 156 is mounted within the main housing 146. The edge card 156 is in the form of a printed circuit board and has a plurality of edge mounted contacts on one edge of the same, preferably the edge facing proximally of the handle 142. Such a printed circuit card in addition to carrying the desired circuitry also includes in the present embodiment a fuse circuit which is embedded in a printed circuit board for controlling or limiting the use of the device as for example for only permitting two uses of the device.

A suitable card edge connector 161 such as a 2 by 10 connector is mounted in the connector housing 147 and is adapted to frictionally engage and electrically contact the edge mounted contacts carried by the edge card 156. As shown particularly in FIG. 8, the edge card 156 is mounted in the proximal end 151 of the main housing 146 whereas the card edge connector 161 is mounted in the distal end 152 of the connector housing 147 so that the connector and edge card can be mated when the main housing 146 and the connector housing 147 are mated or interconnected. The card edge connector 161 is connected to another printed circuit card 162 in a conventional manner and is connected by electrical conductors (not shown) to a flexible cable 163 extending into the connector housing 147 and extending proximally therefrom. The distal extremity of the cable 163 and the printed circuit board 162 are encased by a custom overmold 166 formed of a suitable plastic insulating material to encapsulate the electrical conductors connecting the cable 163 to the connector 161. The overmold 166 also has a portion 166a which extends proximally from the connector housing 147 to provide a strain relief for the cable 163.

In the main housing 146, the proximal extremity of an elongate flex circuit 171 is secured to and connected to the circuitry carried by the edge card 156. The distal extremity of the elongate flex circuit 171 is secured physically and electrically to a PC board 172.

A needle 176 has its proximal extremity secured to the underside of the PC board 172 by a metal clasp 177 to firmly hold the needle. The needle 176 is provided with a fixed insulating sleeve 178 so that an exposed sharpened distal extremity 176a is provided on the needle. The needle 176 can carry one or more thermocouples of the type hereinbefore described in connection with the previous embodiments. The needle and thermocouples carried thereby are electrically connected on the PC board 172. Electrical connections extend from the PC board 172 through the flex circuit 171 to the fuse circuit carried by the edge card 156 and thence through the cable 163 to the radiofrequency power supply and controller of the type hereinbefore described.

Figure 9:
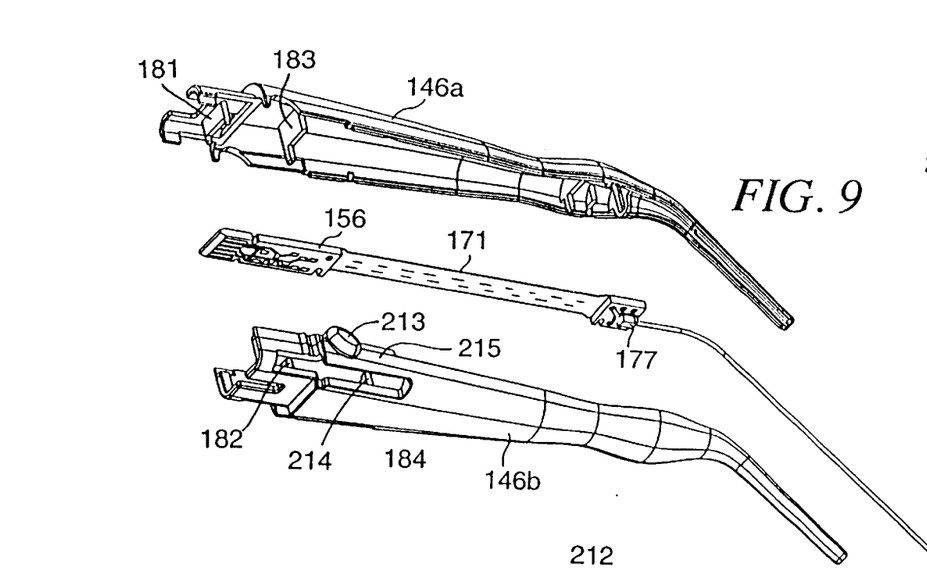
FIG. 9 is an exploded view of a portion of the device as shown in FIGS. 7 and 8.
Figure 10:
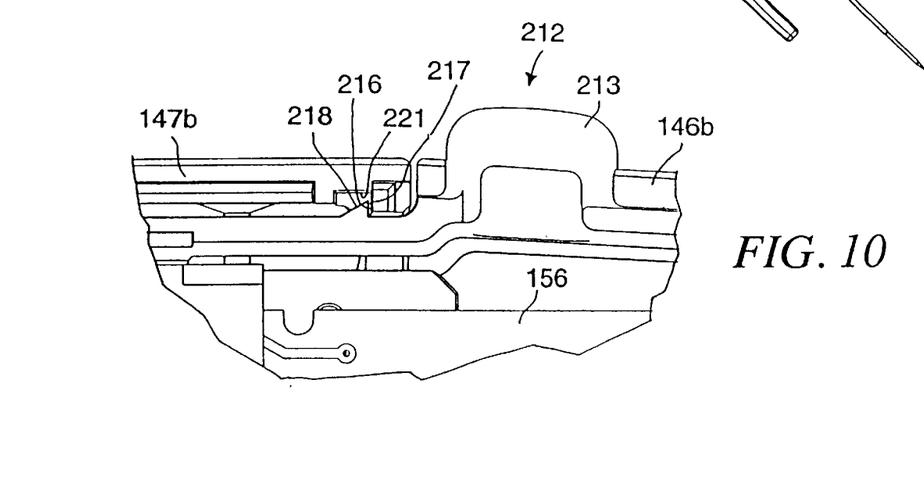
FIG. 10 is an enlarged cross-sectional view showing the manner in which the two parts of the device as shown in FIG. 7 and 8 are detachably secured to each other.

As shown in FIGS. 8 and 9 of the drawings, the top and bottom casings 146a and 146b are provided with support means for supporting the edge card 156 and the PC board 162 in a firm position within the main housing. Such means consists of pairs of support pedestals in which one pair consists of mating support pedestals 181 and 182 and the another pair consists of support pedestals 183 and 184 spaced from the first pair. One of the pedestals of each pair is provided with a U-shaped recess 186 which is sized to accommodate the edge card 156 for supporting the edge card 156 in a firm position so that it can be readily engaged and disengaged by the card edge connector 161 carried by the connector housing 147. Similar support means is provided for the PC board 172 and consists of mating support pedestals 187 and 188 supporting one end of the PC board 172 and support pedestals 191 and 192 supporting the other end of the PC board 172 and the proximal end of the needle 176 secured thereto. A cross member 193 forms a part of the lower casing 146b and extends transversely of the bottom casing 146b and serves to support the flex circuit 171 in a region intermediate the PC board 172 and the edge card 156.

The needle 176 is formed of a suitable material such as a nickel-titanium alloy and has a suitable length as for example approximately 4" and a suitable diameter as for example 0.0026". The insulating sleeve 178 provided on the needle 176 extends to near the tip 176a of the needle 176 but leaving a portion exposed as for example 15 mm from the sharp needle tip. Typically one of the thermocouples is carried by the tip whereas the other thermocouple is carried at the distal extremity of the insulation layer 176 as hereinbefore described.

The main housing 146 has a generally tapered appearance. It has a taper which extends down into a circular necked-down region 201 after which distally there is provided a spherical bulge 202. This necked-down region 201 and the spherical bulge 202 provide a region to facilitate gripping of the handle 142 between two fingers of the hand as for example the thumb and forefinger. After the bulge 202, the main housing 146 is provided with a tapered inclined region 203 and thence distally a tapered generally cylindrical region 204 of a smaller diameter which encloses the needle as it extends from the printed circuit board 172 as shown particularly in FIG. 8. In this configuration, the cylindrical region 204 extends at an angle of approximately 45° with respect to the main portion of the main housing 146. This inclination is provided to provide high visibility to the physician using the device as hereinafter described for viewing the cavity areas where the device is being used.

A bracket 206 is provided within the top casing 146a and is formed integral therewith. The bracket 206 is provided with a hole 207 therein through which the needle 176 extends. A hole 208 is provided in the top casing 146a in the vicinity of the bracket 206 and permits viewing of the proximal extremity of the needle 176.

Cooperative attachment means is provided for removably securing the connector housing 147 to the main housing 146 and consists of side latches or detents 211 and 212. Each of the side latches or detents consists of a raised protrusion 213 serving as a button adapted to be engaged by a finger of the hand. The raised protrusion 213 is formed integral with the bottom casing 146b. An elongate slot 214 (see FIG. 9) is provided in the proximal extremity of the lower casing 146b and extends in both directions from the protrusion 213 so that the portion 215 of the bottom casing 146b immediately underlying the raised protrusion 213 can be pressed inwardly to cause deflection of that part of the housing and to cause inward movement of a protrusion 216 carried thereby which is triangular in cross section. The protrusion 216 is provided with a vertical face 217 which extends generally parallel to the direction of movement of the portion 215 as it is depressed by the raised protrusion 213 (see FIG. 10) and at an angle with respect to an inclined surface 218. This triangular-shaped protrusion 216 is adapted to be received by a recess 221 provided in the bottom cover 147b of the connector housing 147. Thus it can be seen by grasping the handle 142 and depressing both of the buttons or raised protrusion 213 with two fingers of the hand and pushing inwardly on the same, the connector housing 147 can be detached from the main housing 146 and the card edge connector 161 separated from the card edge connector 161. Similarly, the connector housing 147 can be attached to the main housing and the card edge connector 161 by relative movement between the connector housing 147 and the main housing 146 which causes the connector housing to cam over the inclined surface 218 while depressing the same to provide clearance until the protrusions 216 can snap into the recesses 221 provided on opposite sides of the bottom cover 147b.

Operation and use of the device 141 shown in FIGS. 7 through 10 is very similar to that hereinbefore described with the previously disclosed embodiments. The device 141 by the use of the cable 163 is connected to the radiofrequency power supply and controller 13 hereinbefore described. The physician desiring to do the tissue ablation procedure grasps the handle 142 of the device 141 by placing the forefinger and a thumb in the necked-down region 201 just proximal of the spherical bulge 202. The physician while holding the device 141 in one hand can readily view the needle 176 and by way of example can advance the needle into the turbinate areas of the nasal passages of the patient. Typically the needle is inserted into the turbinate with its sharpened distal extremity 176a penetrating the tissue so that the exposed area is disposed within the tissue and the insulating layer 178 penetrates at least slightly below the surface of the tissue being penetrated. Radiofrequency energy can then be applied to accomplish the desired ablation procedure. After the ablation procedure has been completed, the device 141 can be removed. If desired, the device can be utilized to penetrate other areas of the tissue to be treated if that is desired.

The device 141 particularly lends itself to such procedures because it is a low cost device. It has a number of unique features which contribute to this cost containment goal. The utilization of an edge card in conjunction with a card edge connector simplifies the connection between the main housing 146 and the connector housing. If desired, the main housing 146 can be discarded after a one time use after separating it from the connector housing 147 as hereinbefore described. This makes it possible to save the cost of replacing the connector housing 147 and its relatively expensive cabling 163. The use of the flex circuit between the edge card 156 and the PC board 172 also greatly simplifies the construction and assembly of the device.

Figure 11:
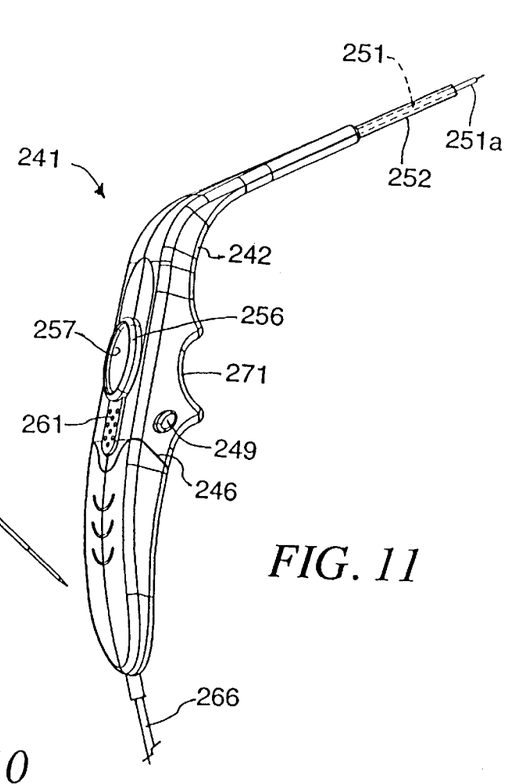
FIG. 11 is an isometric view of still another embodiment of the present invention.

Another embodiment of a device incorporating the present invention is shown in the device 241 in FIG. 11. As shown therein, this device 241 is comprised of a main housing 242 and a connector housing 243 which are constructed in a manner similar to the main housing 146 and the connector housing 147 with differences in the outer and inner configurations. The main housing 242 has the connector housing 243 connected thereto in a manner as hereinbefore described in conjunction with the device 141 and can be separated along a parting line 246 to provide separation between a card edge connector (not shown) provided in the connector housing 243 and connected to an edge card (not shown) in the main housing 242. Raised protrusions 249 are provided on opposite sides to facilitate the connection and disconnection of the two housings 242 and 243 and correspond to the protrusions 213 provided in the device 141.

A retractable needle 251 is slidably mounted in the main housing 242 for movement between extended and retracted positions and which in the retracted position is enclosed within the main housing 242. The retractable needle is provided with a sharpened tip 251a which is exposed for a suitable distance as for example 15 mm with the remaining part being covered by an insulating layer 252. The retractable needle 251 is mounted on a PC board (not shown) similar to the PC board 172 which is carried by a slider (not shown) corresponding to the slider 122 shown in FIG. 6 which is connected to an oval-shaped knob 256 through an extension (not shown) that travels in a slot such as slot 123 in FIG. 6. The knob 256 is provided with an upwardly facing oval-shaped recess 257 provided on the knob 256 and which is adapted to be engaged by a finger of the hand as for example the forefinger while the remainder of the hand is being utilized for holding the device 241. The device 241 is provided with a tab 261 which covers the slot (not shown) in the main housing so that it remains invisible as the knob 256 is advanced and retracted during advancement and retraction of the retractable needle 251.

The connector housing 243 is provided with a cable 266 of the same type as cable 163 hereinbefore described in conjunction with the embodiment shown in FIGS. 7 through 10.

The device 241 has a main housing 242 and a connector housing 243 sized is such a manner so that the device can be readily held in the palm of a human hand. The main housing 242 is provided with an arcuate transversely disposed recess 271 which can be readily be grasped by the forefinger of the hand holding the device while at the same time permitting the thumb of the same hand to be inserted into the recess 257 to translate the knob 256 longitudinally of the main housing for causing extension and retraction of the retractable needle 251. The device 241 can be utilized for ablation procedures of the type hereinbefore described as for example for deployment of the needle 251 into the uvula, soft palate and into the tongue regions of the oral cavity. If desired, the retractable needle 251 can be formed of a nickel-titanium alloy so that it can be provided with a memory which returns to a straight shape even after it has been bent. For the device as shown in FIG. 11 it may be desirable to provide a needle 251 which can be bent. If that is the case, it is desirable that a material other than a nickel-titanium alloy such as stainless steel be utilized so that this makes it possible for the physician using the device to preshape the curvature of the needle before commencing the procedure or after commencement of the procedure in more difficult to reach regions.

From the foregoing it can be seen that there has been provided a device which can be utilized for ablation of tissue in connection with a radio frequency power supply and controller. The devices are small and adapted to be held by the human hand and are designed in such a manner so that the entire device or only a portion of the device can be disposed of after a one-time use. Static or retractable needles can be provided. The construction has been kept so that it is relatively simple to minimize the cost of construction and inexpensive materials have been utilized where possible.

What is claimed:

1. A device for the ablation of tissue for use with the fingers of a human hand and a radio frequency power supply and controller providing a source of radio frequency energy and means for controlling the application of radio frequency energy to the device comprising a handle sized so that is adapted to be grasped and supported by the human hand and having proximal and distal extremities, a single conductive needle formed of a conducting material and disposed in the distal extremity of the handle, an edge card mounted in the handle and having edge mounted contacts with circuitry connected thereto, an edge mount board connector mounted in the handle and removably secured to the edge mounted contacts of the edge card, a cable connected to said connector and extending from the proximal extremity of the handle and being adapted to be coupled to the radiofrequency power supply and controller, a second printed circuit board mounted in the handle in a spaced-apart position from the edge card and a flex cable having conductive leads carried thereby extending between the edge card and the printed circuit board and being physically connected to the edge card and the printed circuit board and making electrical connections therewith, said conductive needle having a proximal extremity and means securing the proximal extremity of the needle to the printed circuit board and making electrical connections therewith.

2. A device as in claim 1 wherein said needle carries at least one thermocouple electrically connected to the printed circuit board.

3. A device as in claim 1 wherein a slider is mounted in said housing and includes said printed circuit board and means extending exterior of the handle adapted to be grasped by a finger of the hand for retracting and advancing the slider to cause advancement and retraction of the needle.

4. A device as in claim 3 wherein advancement and retraction of the needle is accommodated by flexing of the flex circuit.

5. A device as in claim 1 in which the handle is comprised of a main housing and a connector housing and in which the edge card and the flex cable are mounted in the main housing and wherein the edge-mount board connector is mounted in the connector housing and cooperative attachment means carried by the main housing and the connector housing permitting attachment and detachment of the connector housing to the main housing.

6. A device as in claim 5 wherein said cooperative attachment means includes protrusions carried on opposite sides of the main housing and adapted to be engaged by fingers of the hand for causing operation of the cooperative attachment means to permit disengagement of the connector housing from the main housing.

7. A device as in claim 6 wherein said cooperative attachment means includes a portion of one of the main housing and the connector housing which carries the protrusion and in which said portion has recesses adjacent thereto to permit flexing of said portion with respect to the one housing to permit engagement and disengagement of the connector housing and the main housing.

8. A device for the ablation of tissue for use with the fingers of a human hand and a radiofrequency power supply in controlling and providing a source of radiofrequency energy and means for controlling the application of radiofrequency energy to the device comprising a two-piece housing in the form of a main housing and a connector housing, cooperative attachment means carried by the two-piece housing making possible the detachment and attachment of the connector housing from and to the main housing, an edge card mounted in the main housing, an edge-mount board connector mounted in the connector housing, a single needle carried by the main housing, a printed circuit board mounted in the main housing, means in the main housing connecting the single needle to the printed circuit board and circuitry within the main housing connecting the printed circuit board to the edge card.

9. A device as in claim 8 wherein said cooperative attachment means includes a recess mounted in one of said main and connector housings and a movable detent portion carried by the other of said main and connector housings for engaging said recess.

10. A device as in claim 9 wherein said movable detent portion forms a part of said other of said main and connector housings and includes a protrusion adapted to be engaged by a finger of the hand externally of said other of said main and connector housings.

11. A device as in claim 10 wherein said movable detent portion has an elongate recess in said other of said main and connetor housings adjacent said detent portion.

12. A device as in claim 8 wherein said printed circuit board is slidably mounted in said main housing and means extending exterior of the main housing adapted to be engaged by a finger of the hand holding the device to cause advancement and retraction of the printed circuit board and the needle carried thereby.

13. A device as in claim 12 wherein said electrical means interconnecting the printed circuit board to the edge card includes a flex circuit.

* * * * *